(12) United States Patent
Boxrud

(10) Patent No.: US 7,288,263 B2
(45) Date of Patent: Oct. 30, 2007

(54) COMPOSITIONS AND METHODS FOR TREATMENT OF SKIN DISCOLORATION

(75) Inventor: Cynthia A. Boxrud, Santa Monica, CA (US)

(73) Assignee: Evera Laboratories, LLC, Santa Monica, CA (US)

( * ) Notice: Subject to any disclaimer, the term of this patent is extended or adjusted under 35 U.S.C. 154(b) by 456 days.

(21) Appl. No.: 11/037,589

(22) Filed: Jan. 18, 2005

(65) Prior Publication Data

US 2006/0057081 A1    Mar. 16, 2006

Related U.S. Application Data

(60) Provisional application No. 60/609,543, filed on Sep. 13, 2004.

(51) Int. Cl.
*A61K 8/00* (2006.01)
*A61K 8/02* (2006.01)
*A61K 8/04* (2006.01)
*A61Q 19/00* (2006.01)
*A61Q 17/04* (2006.01)

(52) U.S. Cl. .......................... 424/401; 424/59; 424/60; 424/400

(58) Field of Classification Search ................ 424/400, 424/401, 145, 148, 59, 60; 514/937, 938, 514/939
See application file for complete search history.

(56) References Cited

U.S. PATENT DOCUMENTS

| 4,285,967 | A | * | 8/1981 | Gubernick et al. ......... 514/653 |
| 4,699,924 | A |   | 10/1987 | Durrant et al. |
| 5,614,178 | A | * | 3/1997 | Bloom et al. ................. 424/60 |
| 6,395,260 | B1 |  | 5/2002 | Ley et al. |
| 6,503,523 | B2 |  | 1/2003 | Hoppe et al. |

OTHER PUBLICATIONS www.feelconfident.co.uk: Circle Clear Article.
www.bydoctorsonly.com/skincare.html—Skin Care Article.

* cited by examiner

*Primary Examiner*—Shelley A. Dodson
(74) *Attorney, Agent, or Firm*—Saliwanchik, Lloyd & Saliwanchik

(57) ABSTRACT

A cosmetically acceptable product for application to human skin is disclosed. The novel compositions are particularly suited for skin lightening and for diminishing the appearance of "dark circles" under the eyes. The compositions include any of several vasoconstrictors in a carrier with optionally added skin compatible ingredients.

24 Claims, 4 Drawing Sheets
(4 of 4 Drawing Sheet(s) Filed in Color)

COMPOSITIONS AND METHODS FOR TREATMENT OF SKIN DISCOLORATION

CROSS REFERENCE TO RELATED APPLICATION

This application claims benefit of U.S. Provisional Application 60/609,543 filed Sep. 13, 2004.

BACKGROUND OF THE INVENTION

1. Field of the Invention

The present invention relates to topical compositions useful for treating skin discolorations and to methods of use for these compositions.

2. Description of the Background Art

Skin discoloration is a common complaint. Discoloration may occur in any location on the body and frequently occurs under the eyes. Often referred to as infraorbital discoloration, it has also been described as "dark circles". Discoloration under the eye usually follows the anatomy of the orbicularis oculi muscle, which surrounds the orbital area. While frequently referred to as a pigmentary condition, the cause of this type of discoloration tends to be multifactorial and is more often the result of a combination of factors including skin translucency, vascularity, and heredity/ethnicity.

Because dark circle discoloration most typically follows the muscle surrounding the orbital area, it has most often been attributed to hyperpigmentation. This is not necessarily the cause in all patients, despite attempts to address infraorbital discoloration as a hyperpigmentation problem in the region of the lower eyelid. Unfortunately, most patients experiencing dark circles have not been examined with respect to identification of the inter-individual anatomic structural elements that can contribute to developing appropriate treatment protocols.

Generally, there are four main categories of causes for dark circles, which can be present in isolation or in combination, including deep vascular congestion/superficial vascularity, hyperpigmentation, skin translucency, and structural shadowing. It is important to differentiate between these various causes in order to appropriately select treatment modalities to achieve a successful outcome.

The rich vascular network located around the medial canthus and nasal periorbital regions is the cause of the appearance of dark circles seen in children and adults with chronic allergies or sinus disease. Typically referred to as "allergic shiners", these bluish discolorations in the orbitopalpebral groove are caused by chrome congestion of the nasal and paranasal cavities.

A complex superficial vascular network exists within the dermis of the eyelid. When these small, subcutaneous vessels become visible they lend a reddish discoloration to the area. Visibility may result from chronic eye rubbing, which creates repeated superficial trauma to the area. Rubbing of the eyes may also lead to deposition of pigment.

Hyper-pigmentation occurs in a semicircular pattern involving the lower eyelid and may result from a multitude of focal or systemic conditions. Post inflammatory hyperpigmentation can cause pigment accumulation in a superficial (more commonly) or deep (severe cases) pattern. Inflammatory conditions that disrupt the deep dermal-epidermal junction often heal with melanin deposition in the dermal macrophages where turnover of melanin is extremely slow. If severe, other types of inflammatory conditions such as allergic dermatitis, trauma, drug eruptions, and photocontact dermatitis can lead to disruption in the dermoepidermal junction.

Hyperpigmentation can also result from non-inflammatory lesions of the peri-orbital area. Examples of these conditions include melasma, ephelides, lentigo simplex, juntional nevi, solar lentigines ("liver spots"), and nevi. Systemic conditions that can lead to pigmentation of the penorbital area include various metabolic and endocrine disorders.

The skin of the eyelids and periorbital area is markedly thin in comparison to skin elsewhere on the face. Additionally, the skin becomes even thinner with aging, causing it to become more translucent. The vascular network underlying the surface becomes visible and lends a reddish-blue hue to the periorbital area. This is especially true in the area of the infraorbital rim where the lack of structural fat and muscle found elsewhere on the face places the coloration in relief against the underlying bone.

Multiple anatomical aspects of the peri-orbital area can create shadows in the infra-orbital area. Classically, deeply set orbits can cause shadowing resulting in discoloration in the infra-orbital area. With prolapse of the infraorbital fat and a prominent naso fugal fold, the double convex contour of the infraorbital area creates a color change, which may be structural and vascular. This contour creates a shadow in the underlying tear trough. Shadows can also occur from other facial structures, such as a steep nasal bridge, prominent frontal bossing deeply set eyes, or enophthalmos.

The skin of the lower eyelid is contiguous with that of the upper cheek/malar area. With aging, the mid-face descends due to loss of support by the lateral component of the orbitomalar ligament and loss of volume. With this descent of the midface, a tear trough deformity is created and therefore a "dark circle".

Exfoliating and bleaching creams have been used to address superficial hyper pigmentation. If examination determines that pigment is superficial, exfoliating creams (such as retinoic acid) and bleaching creams (containing hydroquinones) have been used to exfoliate and lighten and lessen pigment deposition. Further addition of an exfoliating agent to the regimen has been reported to result in a synergistic effect. Unfortunately, use of hydroquinone is not always successful in fading lesions and in most cases the original discoloration returns.

Regardless of the source of the pigment, it usually takes a minimum of three weeks to a few months before results are visible. Furthermore, in preparations containing hydroquinone, the higher the concentration of hydroquinone, the greater the incidence of side effects, such as dermatitis. Combination treatments with an added corticosteroid cream have sometimes been used to decrease the incidence of dermatitis; however, caution must be taken with prolonged use of corticosteroids on the face, because telangiectasia, atrophy or acne rosacea may develop. Skin atrophy may also be an issue in the already thin skin of the periorbital region.

Allergic reactions are always a consideration for agents applied directly to the skin. It is therefore important to patch test for allergy with hydroquinones. Additionally, sun exposure must be kept to a minimum with tretinoin and hydroquinones and patients are advised to use sunscreen, sunglasses and hats on a regular basis.

Intense Pulsed Light (IPL) utilizes specific wavelengths of light directed to a small area to accomplish its effect. IPL can improve a variety of benign skin imperfections such as superficial and deeper pigment, telangectatic changes of the skin (such as with rosacea), and even unwanted hair.

Chemical peels have been used to treat dark circles mainly attributed to hyperpigmentation. A variety of solutions may be used to perform chemical peeling, including (in increasing order of strength): trichloroacetic acid 35%, trichloroacetic acid 50%, phenol 89%, and Baker's phenol formula. The stronger the chemical, the deeper the peel with greater effects but with increasing risk and longer recovery.

Potential side effects of chemical peels include erythema, infection, hypopigmentation, cicatricial eetropion, scarring, ocular damage, and splotchy hyperpigmentation.

Laser therapy targets hyper pigmentation in the infraorbital area. Little has been reported in the area of pigment-targeted laser treatments for dark circles.

Electro-Optical Synergy technology (ELOS™) is a recent advance in the treatment of pigmented and vascular dyschromia. The theory behind this new technology stems from the theoretical limits of the light based technologies. Combining two types of energies, optical and electrical, (conducted radiofrequency) allows the use of less optical energy at a level that is safe even for dark skin.

The role of surgical intervention in treating skin discolorations is primarily targeted to treating the structural causes of dark circles, such as shadowing from inferior orbital herniated fat, malar hypoplasia, and/or tear trough deformity. These conditions, either in isolation or in concert, can be treated by lower eyelid blepharoplasty with or without fat transposition, meoplication, midface elevation, and/or facial fat injections. Each is addressed with differing or multiple procedures depending on the patient's underlying structure.

There are a multitude of skin products on the market, many with claims to reduce the appearance of skin discolorations, particularly "age-spots." Eye care preparations are particularly popular, and include products by almost every major cosmetic company. Some contain hydroquinones, but most include various humectants and skin softeners. An example of a product that touts use of all-natural ingredients is a "Restorative Eye Gel" containing botanical extracts including Butcher's Broom, Horsechestnut, D-beta glucosamine and Spin Trap™. One of the ingredients, the Butcher's Broom Extract, is said to have a vasoconstrictor effect by purportedly strengthening capillary walls, while the combination of extracts is said to reduce puffiness and prevent further skin aging (Bydoctorsonly cosmetic products).

Methods for treating and preventing undesired pigmentation of the skin are described in U.S. Pat. No. 6,503,523, where the compositions include vitamin A related compounds in combination with various ubiquinones.

DEFICIENCIES IN THE ART

Although there are numerous modalities, including surgery, for treatment of dark circles under the eyes, many of the methods are not suitable for long-term use and some have undesirable side effects, such as skin irritation. Additionally, of the multitude of cosmetic preparations available, few are truly effective. Those that contain hydroquinones are not ideal because of side effects.

Accordingly, there is a need for safe and effective compositions that are especially suitable for ameliorating the appearance of dark circle type discoloration under the eyes.

SUMMARY OF THE INVENTION

A surprisingly effective topical composition for treating skin darkening has been discovered and shown to be particularly successful in improving the appearance of dark circles in the suborbital region. Skin-lightening compositions have been developed, which comprise ophthalmic vasoconstrictors and/or their inorganic or organic salts, which may be combined with a variety of other agents for topical administration. The novel compositions are particularly advantageous for use on the face to lighten darkened skin and to improve the appearance of "dark circles" under the eyes.

The invention also includes use of the disclosed compositions for treating darkened areas on the skin, particularly the face, neck and hands. Other parts of the body, including legs and arms may also benefit when darkening from injury, sun damage or other insult is treated with the new compositions. A particularly advantageous feature of the invention is the option to use it over relatively long periods of time because the ingredients are commonly recognized as non-toxic for skin applications.

The invention comprises cosmetically acceptable compositions having as a key active ingredient a vasoconstrictor or vasoconstrictor salt. The compositions are formulated in a pharmaceutically acceptable carrier that preferably includes pharmaceutical grade vasoconstrictors.

The vasoconstrictors may be in the form of inorganic or organic salts, recognizing that the cationic moiety of the vasoconstrictor may be, for example, naphazolinium ion in combination with a negative counter ion. While hydrochloride salts may be most convenient, this should not exclude consideration of other salts such as corresponding sulfates, phosphates or other inorganic non-toxic physiologically compatible salts.

Organic salts of the vasoconstrictors are believed to be highly preferable, including lactates, glycolates, citrates, maleates, salicylates, malates and tartrates. Although higher in cost, certain vasoconstrictor organic salts offer additional advantages by virtue of emollient and skin penetration properties. For example, some are excellent exfoliating agents while others may facilitate penetration of the stratum corneum barrier layer of the skin, thereby contributing to increased effectiveness of the vasodilator skin lightening effect.

Examples of vasoconstrictors that may be used in the disclosed formulations include tetrahydrozoline, ephedrine, naphazoline, phenylephrine, pheniramine and their salts, with tetrahydrozoline and naphazoline salts being particularly preferred. Mixtures of different salts of the vasoconstrictors, organic and inorganic, may be employed. In preparing the formulations, the vasoconstrictors may be used directly, as a salt may form by addition of other ingredients and/or by adjustment of pH in aqueous carriers.

The amount of vasoconstrictor or vasoconstrictor salt to be used may be varied with preferred amounts comprising 0.005% to 7.5% by weight, preferably 0.01 to 5.00% by weight and most preferably about 4% by weight. Of course the amount may depend on the additional ingredients in the composition. For example, lesser amounts would be required when highly efficient skin penetrants are part of the formulation.

Carriers may be based on an aqueous gel, anhydrous gel, a water-in-oil emulsion, an oil-in-water emulsion, or water. Examples include purified water, dimethicone, triethanol amine, phenoxyethanol, benzene free carbomer, phenoxyethanol, benzene free carbomer, methylparaben, isopropylparaben, ispropylparaben, isobutylparaben, and butylparaben.

Most compositions will preferably include an emollient, a neutralizer-thickener, and/or a preservative. Preservatives are usually added in order to increase shelf life and are used in numerous cosmetic preparations intended for use over a period of time and which tend to be stored at or above room temperature. Neutralizers may be used to adjust pH, which for skin preparations is preferably on the acidic side below pH 7, often in the range of pH 3.5-4.0. Thickeners, also well known in the art, may be added for texture and convenience in application.

Emollients are often included in cosmetic preparations to enhance penetration of active ingredients. Organic acids are particularly desirable for use in the disclosed formulations because they act not only as emollients but are also good exfoliators. These effects can be obtained by using the organic salts of the vasoconstrictors.

There are a number of other agents that can be combined with the vasoconstrictors used in the disclosed formulations, including vitamins and sunscreens. Vitamins found in many commercial face creams include vitamins A, E, C, D, F, $CoQ_{10}$. These may be added alone or in combination for possible anti-oxidative benefits.

Sunscreen agents include p-aminobenzoic acid, paraben, digalloyl trioleate, dioxybenzone, ethyldihydroxy propyl PABA, ethylhexyl p-methoxycinnamate, ethylhexyl salicylate, glyceryl PABA, homosalate, menthyl anthranilate, octocrylene, octyl methoxycinnamate, octyl salicylate, oxybenzone, octyl dimethyl PABA, red petrolatum, titanium dioxide and zinc oxide. These additional ingredients are often used in skin preparations to protect against UV exposure; however, care must be used in the selection as not all protect against UVA and some may cause skin irritation.

The new compositions may also be formulated to combine with customary make-up formulations, such as under-eye concealer and customized liquid formulations for different skin color.

The compositions of the present invention are effective for treating skin discolorations, particularly on the face, and most particularly under the eye for conditions commonly described as Dark Circles. Other conditions that may benefit from application of the composition include skin discolorations arising from excess pigmentation, light damage, physical trauma and disease.

Treatments include topical application of the disclosed compositions to the affected area. The number of applications and the length of time to continue treatment will vary according to the individual. In most cases there is an almost immediate visible effect but in general improvements will be observed after 6-8 hours. Applications are conveniently based on a twice daily schedule and can be continued for up to 6-8 weeks. It may be possible to discontinue use after a period of time; however, it is believed that treatments should be continuous for optimal results.

BRIEF DESCRIPTION OF THE DRAWINGS

The patent application file contains at least one drawing executed in color. Copies of this patent or patent application publication with color drawing(s) will be provided by the Office upon request and payment of the necessary fees.

FIG. 1. Photographs showing typical results of treatment of the left under eye region.

FIG. 2. Photographs showing results of treatment of the left under eye region of a non-Caucasian female subject.

FIG. 3. Photographs of a young Caucasian female showing results of the disclosed treatment.

DETAILED DESCRIPTION OF THE INVENTION

Figure 1A:
FIG. 1A shows a female Caucasian subject before treatment of the under eye region.

The present invention provides a surprisingly effective method for treating certain types of dark circles in the orbital region. Highly absorbed topical compositions comprising a vasoconstrictor salts such as tetrahydrozoline hydrochloride, ephedrine hydrochloride, naphazoline hydrochloride, phenylephrine hydrochloride, pheniramine maleate and mixtures thereof, have been shown to lessen dark pigmentation of the skin, with dramatic results in some cases. The compositions are particularly effective for 'dark circles' under the eyes and for treating darkened skin caused by vascular conditions. Certain types of hyperpigmentation can also be effectively treated and lightened skin tone may also result in improvements in skin translucency.

The active ingredient is the vasoconstrictor, which is preferably in the range of 0.005 to 7.5% and more preferably in the range of 0.01-5.00%. Of course formulations may be adjusted depending on the nature of the formulating vehicle, since this may affect how much and how quickly the active agent is absorbed.

The vasoconstrictor is best absorbed as a salt, which may be inorganic or organic. Inorganic salts, as discussed, include hydrochlorides, sulfates, phosphates and the like, while exemplary organic salts may include lactates, citrates, maleates, salicylates such as would be expected to penetrate the stratum corneum barrier layer. In view of the cost and availability of the various organic salts of the disclosed vasoconstrictors, it may be preferable to use combinations of organic and inorganic salts of these compounds.

In preparing an exemplary composition, one may admix salicylic acid, glycolic acid and/or lactic acid with a solution of one or more inorganic vasoconstrictor salts to provide a composition expected to exhibit increased skin penetration thereby contributing to greater product efficacy. An additional benefit of incorporating the salts of glycolic, lactic, citric, malic and/or tartaric acids is that with proper adjustment of pH in the range of 3 to 7, these salts act as skin moisturizers, thereby incorporating skin softening with benefits from the action of the vasoconstrictor. A further benefit arising from adding one of these organic salts are their well-known skin exfoliating properties, which help in removing layers of dead cells in the stratum corneum, which further enhances vasoconstrictor penetration.

The compositions are cosmetically acceptable and will be convenient for topical application. The compositions will be comprised in a carrier, which may be inert, or, preferably combined with other agents that enhance absorption of the vasoconstrictor.

Carriers may be an aqueous or anhydrous gel, a water-in-oil emulsion, an oil-in-water emulsion, or an aqueous solution. It may also be advantageous to adjust pH for water-based carriers, using physiologically compatible buffers including simple inorganic buffers such as phosphate or borate. Inert carriers may comprise water, an emollient, a neutralizer-thickener and a preservative or mixture of preservatives. Suitable preservatives include mixtures of the lower alkyl parabens, hydantoins, diazolidinyl urea, paraben DU and certain natural ingredients such as grapefruit seed extract.

Preferably, formulations will comprise skin penetration enhancers such as DMSO, ethyl alcohol, isopropyl alcohol, propylene glycol, butylene glycol, ethoxydiglycol, dimethylisosorbide, 5-fluorouracil and the like. In formulations comprising organic salts of the vasoconstrictors, benzyl alcohol, alpha-bisabolol and/or ethyl alcohol may be included to enhance penetration of the stratum corneum.

Where application is to dry or older skin, it may be preferable to avoid alcohols and to employ skin enhancers that have moisturizer properties and/or because they may be less irritating than the alcohol enhancers. Examples include alkyl esters, menthol derivatives and phospholipids such as unsaturated glycerol monoethers, alpha-linoleinic acid, linoleic acid, cod liver oil, menthol, ethyl ether derivatives of menthol, squalene and herbals such as chamomile flavones, apigenin, luteolin and apigenin-7-O-β-glucoside. Skin penetration enhancers may also be selected to optimize vasoconstrictor absorption within a desirable period of time; for example, for night treatments where 7-8 hour continuous treatment is expected to be beneficial.

Skin moisturizers may also be included in the disclosed formulations. Exemplary and commonly used moisturizers include glycerin, sodium hyaluronate, propylene glycol, lactate salts, urea, amino acids, and the like. These ingredients may be used singly or in combination with each other or with water insoluble moisturizers such as mineral oil, petrolatum, vegetable oils, synthetic organic esters, which may include cetyl isostearate, caprylic/capric triglyceride, isopropyl palmitate and the like. Other popular emollients include aloe vera, castor oil, almond oil, cacao butter, shea butter, triglycerides and jojoba.

Depending on the formulation, an emulsifier may be added. Examples include cetyl alcohol, dimethicone, glyceryl stearate and sodium lactate. Some of these compounds also have emollient as well as emulsifying properties and so may serve more than one purpose in the formulations.

Gellants may also be included in the formulations. These agents are typically non-ionic or cationic polymers such as hydroxyethyl cellulose, methylcellulose, guar gum, xanthan gum, hydroxypropylcellulose and cationic cellulosics. A particular example is Sepigel.

Anionic gellants such as carbomer would not be desirable for use in the formulations because of combination with the positively charged vasodilator, and would hinder release of the vasodilator into the skin. In the same manner, care must be taken if the emulsion vehicle is not cationic or non-ionic so that the active ingredients are not inactivated or insolubilized. However, anionic additives may in certain formulations be considered if the release into the skin has the effect of timed release, which may be appropriate.

There are several optional ingredients that may be added to the formulation, including any of a number of fragrances, which may be selected in accordance with a targeted market. Special formulations for men may for example include a fragrance more popular with males than females. Teen-age females may find a strong, flowery fragrance more desirable.

Other optional ingredients include various vitamins and skin sun protection compounds. Sunscreens are popular additions to topical formulations applied to exposed skin; examples include p-aminobenzoic acid, paraben, digalloyl trioleate, dioxybenzone, ethyldihydroxy propyl PABA, ethylhexyl p-methoxycinnamate, ethylhexyl salicylate, glyceryl PABA, homosalicylate, menthyl anthranilate, octocrylene, octyl methoxycinnamate, octyl salicylate, oxybenzone, octyl dimethyl PABA, red petrolatum, titanium dioxide and zinc oxide.

Typical vitamins frequently added to skin preparations include vitamins E, C or F.

There are of course a wide range of optional ingredients that may be added to the disclosed vasoconstrictor compositions, some of which will depend on the age group and the living environment of the product purchaser. For example, different moisturizers may be preferable for formulations sold in Canada, while the Sunbelt state residents may prefer less greasy compositions. Regardless, the art of formulating for different characteristics is well-known and can be readily practiced in consideration of the market. Basic formulations will include at least some skin penetration agent in the excipient or carrier in order to assure a rapid effect on the underlying small blood vessels that cause the skin discoloration.

A typical composition comprises, by weight, purified water from about 5% to 95%, a vasoconstrictor from about 0.005% to 5%, an emollient from about 0.05% to 15%, a neutralizing agent/thickener or gellant from about 0.05% to 5.5%, emollients from 1-25%, and preservatives from about 1% to 3%. Trace amounts of vitamins, such as vitamin E, C and/or F may be added, from about 0.02% to about 1%. A skin sun protector may also be added, such as zinc oxide or titanium dioxide, from about 0.02% to about 1%.

The treatment composition is applied by spreading on the affected area and rubbing it into the skin. The treatment may be applied from once to three times per day, or more if desired, and can be continued as long as improvement occurs. No negative side effects have been observed in the use of the treatment composition. Once treatment is stopped, after a period of time the darkened skin may recur and treatment will have to be resumed.

A careful assessment, requiring a patient history with identification of the inter-individual anatomic structural elements is the key to obtaining an accurate diagnosis. This information can then be incorporated into appropriate treatment protocols.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or composition are to be considered to fall within the scope of the invention disclosed herein.

EXAMPLES

Example 1

Preliminary Studies 45 female subjects complaining of dark circles under their eyes were examined and determined to be appropriate candidates for testing the disclosed compositions. The examination revealed that their 'dark circles' appeared to be caused by vascular changes. An extensive history and physical was completed for the 45 patients who presented with dark circles. 54% were judged to have pigment deposition contributing to the development of the 'dark circles' whereas 82% were diagnosed with a predominantly vascular component.

A cream composition, formulated generally as described in Tables 1-6, was applied to the under eye region of 45 patients. The results demonstrated that infra-orbital discoloration is multifactorial as evidenced by the presence of "discoloration" in both pigmented and non-pigmented individuals. Additionally, the discoloration in the lower eyelid of more pigmented patients was not synonymous with the presence of excess pigment in the area. Many of the more darkly pigmented patients were judged to have 'dark circles' due to a predominantly vascular component. It was concluded that infra-orbital discoloration is more often the result of vascular causes than pigment deposition.

Example 2

This example included a group of 20 female subjects, 18 to 60 years of age, who participated in a study using the disclosed cream. The group included one Hispanic, one Italian and 18 Caucasians. Each subject applied a cream formulation containing tetrahydrozoline to the suborbital area around the left eye. All subjects were photographed before and after completing the treatment regimen. The results were evaluated objectively by color from the photographs of each subject. Improvement to the treated skin color was judged on the average to be at least 20%, based on color loss. Treatment composition effects were found to last for about 6 to about 8 hours after application.

Figure 1B:
FIG. 1B shows results of treatment after the new composition was applied under the left eye. No treatment was applied under the right eye.

Exemplary results are shown in FIGS. 1-3. A typical result is shown in FIG. 1 where FIG. 1A shows the subject before treatment. FIG. 1B shows the eye region of the subject after treatment around the left eye only.

Figure 2A:
FIG. 2A shows the subject before treatment of the under eye region.
Figure 2B:
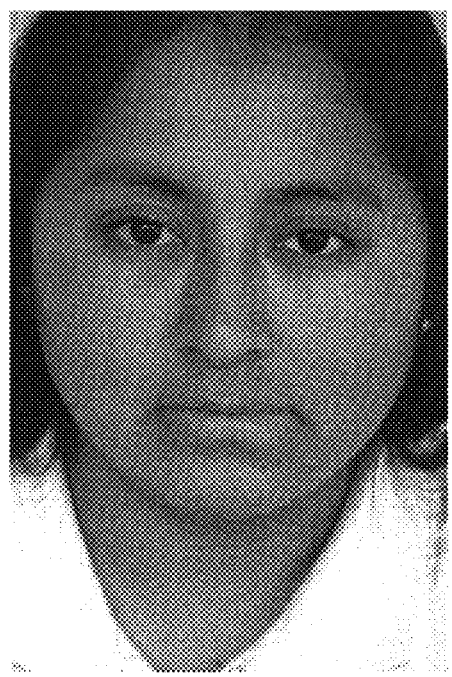
FIG. 2B shows results of treatment after the new composition was applied under the left eye. No treatment was applied under the right eye.

Visible improvement is also shown in the Caucasian subject shown in FIG. 2. The photo in FIG. 2A shows the subject before treatment. FIG. 2B shows results after treating the left eye only. There is a detectable lightening of the dark area around the eye.

Figure 3A:
FIG. 3A shows the subject before treatment of the under eye region.
Figure 3B:
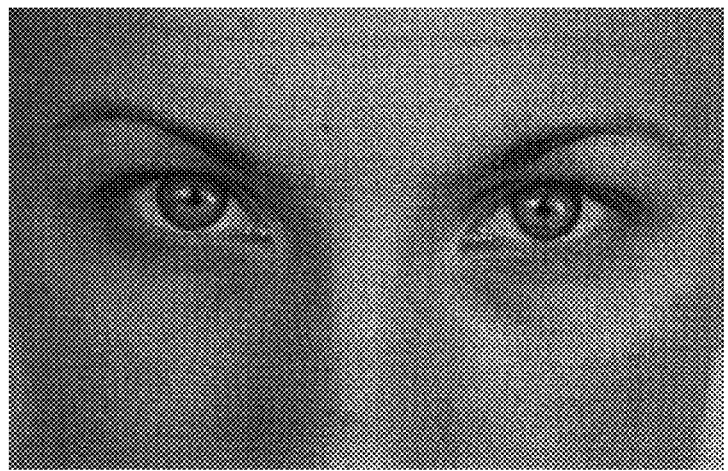
FIG. 3B shows results of treatment after the new composition was applied under the left eye. No treatment was applied under the right eye.
Figure 3C:
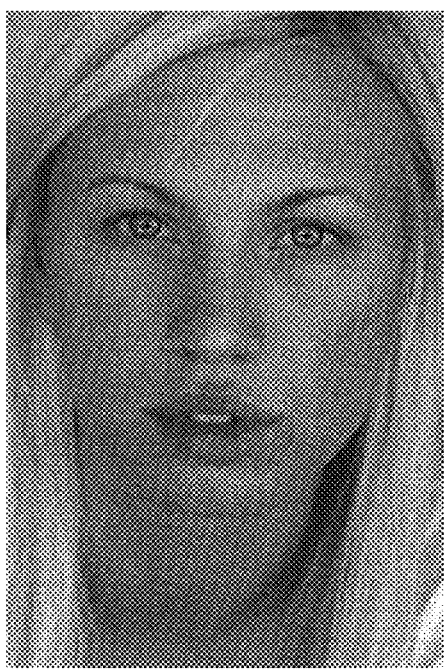
FIG. 3C shows the subject's face before treatment with the new composition.
Figure 3D:
FIG. 3D shows the subject's face after the face was treated showing a distinct improvement in the blotchy discolorations.

FIG. 3 is a series of photographs showing results of treatment under the area of the left eye, FIG. 3B, compared with no treatment, FIG. 3A. Treatment of the face before (FIG. 3C) and after (FIG. 3D) shows a lightening effect.

Example 3

In another group of 25 subjects, 15 females and 10 males ages 25-52 were treated with the new composition, formulated substantially as in Table 2. The formulation was placed on the lower right eyelid. A scale of 1-10 was used to assess the subjective change under the eyelid and improvement in the darkness of the area. Subjects were asked to subjectively rate the results on a scale from 1-10 with 10 being the most improved. All subjects stated that the right eye improvement compared to the left eye control was at least 5 on a scale rating of 5.

Table 1 shows the results with a 20-patient group of 15 females and 5 males, again administering the cream under the right eye. After a 10-minute period, the subjects were asked what percent improvement under the right eye, if any, they perceived compared with the left eye.

TABLE 1

| Subject | Improvement (%) | Sex | Age | Nationality |
|---|---|---|---|---|
| 1(LR) | 40 | F | 22 | Caucasian |
| 2(LS) | 70 | F | 24 | Caucasian |
| 3(CB) | 30 | F | 50 | Caucasian |
| 4(HW) | 10 | F | 57 | Caucasian |
| 5(MB) | 20 | M | 55 | Middle East |
| 6(JW) | 60 | F | 30 | Caucasian |
| 7(SB) | 80 | F | 27 | Caucasian |
| 8(KI) | 50 | M | 35 | Asian |
| 9(FS) | 30 | M | 55 | Caucasian |
| 10(KK) | 70 | F | 50 | Caucasian |
| 11(WP) | 60 | F | 44 | Caucasian |
| 12(SM) | 50 | F | 42 | Caucasian |
| 13(JP) | 40 | F | 13 | Caucasian |
| 14(KF) | 30 | F | 13 | Caucasian |
| 15(TF) | 40 | F | 45 | Caucasian |
| 16(SP) | 50 | M | 56 | Caucasian |
| 17(MT) | 60 | F | 44 | Caucasian |
| 18(JW) | 40 | F | 38 | Caucasian* |
| 19(TH) | 30 | M | 53 | Caucasian |
| 20(JR) | 40 | F | 29 | Hispanic |

*Burning Pt with severe allergies to creams

The average improvement was 44% with the females averaging 45% and the males 25%. Objective photo data was not quantitatively assessed for this group but several patients exhibited a definite improvement in appearance. Results were more notable in younger patients who exhibited a younger appearance and a decrease in wrinkles in the "crow's feet" area around the eye.

Example 4

Exemplary topical formulations. The following tables set forth exemplary formulations that can be employed in the treatment of skin discoloration and which are particularly useful in ameliorating the appearance of dark circles.

TABLE 2

| Ingredient | % by Weight |
|---|---|
| Purified water | 94.56 |
| Tetrahydrozoline hydrochloride | 2.00 |
| Dimethicone | 1.00 |
| Triethylol amine(TEA) | 1.00 |
| Phenoxyethanol | .50 |
| Carbomer (benzene free) | .50 |
| Methylparaben | .20 |
| Isopropylparaben | .10 |
| Propylparaben | .10 |
| Isobutylparaben | .02 |
| Butylparaben | .02 |

TABLE 3

| Aqueous Gel | |
|---|---|
| Naphazoline Hydrochoride | 0.10% |
| Propylene Glycol | 5.00 |
| Ethoxydiglycol | 5.00 |
| Ethyl Alcohol | 5.00 |
| Hydroxypropyl Cellulose | 2.00 |
| Water           qs | 100.0 |

TABLE 4

Oil-In-Water Cationic Emulsion

| | | |
|---|---|---|
| Phenylephrine hydrochloride | | 0.25% |
| Glycerin | | 5.00 |
| Propylen Glycol | | 5.00 |
| Dimethylisosorbide | | 3.00 |
| Ethoxydiglycol | | 5.00 |
| Glyceryl Stearate | | 3.00 |
| Stearyldimonium Chloride | | 2.00 |
| Cetyl Alcohol | | 1.00 |
| Safflower Oil | | 1.00 |
| Sodium PCA | | 1.00 |
| Isocetyl Stearate | | 2.00 |
| Water | qs | 100.00 |

TABLE 5

Oil-in-Water Nonionic Emulsion

| | | |
|---|---|---|
| Tetrahydrozoline hydrochloride | | 2.00% |
| Ephedrine hydrochloride | | 0.50 |
| Glyceryl Stearate | | 3.00 |
| Cetyl Alcohol | | 1.50 |
| Jojoba Oil | | 3.00 |
| Cetearyl Alcohol and Ceteth-20 | | 5.00 |
| Propylene Glycol | | 5.00 |
| Dimethylisosorbide | | 3.00 |
| Ethoxydiglycol | | 5.00 |
| Glycerin | | 5.00 |
| Sodium PCA | | 2.00 |
| Water | qs | 100.00 |

TABLE 6

| | | |
|---|---|---|
| Naphazoline lactate | | 2.50% |
| Pheniramine salicylate | | 2.50 |
| Propylene Glycol | | 5.00 |
| Dimethylisosorbide | | 3.00 |
| Ethoxydiglycol | | 5.00 |
| Glycerin | | 5.00 |
| Sodium PCA | | 2.00 |
| Water | qs | 100.00 |

TABLE 7

| | | |
|---|---|---|
| Naphazoline.HCl | | 2.50% |
| Pheniramine.HCl | | 2.50 |
| Lactic Acid | | 2.00 |
| Glycolic Acid | | 2.00 |
| Salicylic Acid | | 2.00 |
| Propylene Glycol | | 5.00 |
| Dimethylisosorbide | | 3.00 |
| Ethoxydiglycol | | 5.00 |
| Glycerin | | 5.00 |
| Sodium PCA | | 2.00 |
| Potassium Hydroxide | qs to pH 3.50 | |
| Water | qs | 100.00 |

Trace amounts of vitamins, such as vitamin E, C, or F and other nutritional supplements, known to be beneficial for the skin may also be added. A skin sun protector, such as zinc oxide may also be added to the formulations in Tables 2-7.

REFERENCES

The following references to the extent that they provide exemplary procedural or other details supplementary to those set forth herein, are specifically incorporated by reference.

U.S. Pat. No. 6,503,523 for "Skin care agents containing combinations of active agents consisting of vitamin a derivatives and UBI- or plastoquinones" Jan. 7, 2003.

Bydoctorsonly cosmetic products, Restorative Eye Gel

U.S. Pat. No. 4,699,924 for "Skin treatment composition" Oct. 13, 1987.

U.S. Pat. No. 6,395,260 for "Topical cosmetic compositions comprising benzaldoximes" May 28, 2002.

The compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods described herein without departing from the concept, spirit and scope of the invention. Other gellants, thickeners, moisturizers, emollients, emulsifying agents, preservatives and skin penetrants known to the cosmetic, pharmaceutical and dermatological arts may be used in addition to those discussed herein.

More specifically it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A cosmetically acceptable composition for topical skin application, comprising a vasoconstrictor pheniramine or a vasoconstrictor pheniramine salt in a pharmaceutically acceptable carrier.

2. The composition of claim 1 wherein the vasoconstrictor pheniramine salt is an inorganic salt or an organic salt.

3. The composition of claim 2 wherein the inorganic salt is selected from the group consisting of chlorides, sulfates, phosphates and mixtures thereof.

4. The composition of claim 2 wherein the organic salt is selected from the group consisting of lactates, glycolates, citrates, maleates, salicylates, malates and tartrates.

5. The composition of claim 4 further comprising a penetration enhancer selected from the group consisting of benzyl alcohol, alpha-bisabolol, ethyl alcohol, DMSO, isopropyl alcohol, propylene glycol, butylene glycol, ethoxydiglycol, dimethylisosorbide, and 5-fluorouracil.

6. The composition of claim 1 further comprising a vasoconstrictor or vasoconstrictor salt selected from the group consisting of tetrahydrozoline, ephedrine, naphazoline, and salts and mixtures thereof.

7. The composition of claim 1 in which the pheniramine vasoconstrictor or pheniramine vasoconstrictor salt comprises 0.005% to 7.5% by weight.

8. The composition of claim 7 in which the vasaconstrictor pheniramine vasoconstrictor or pheniramine vasoconstrictor salt comprises 0.01 to 5.00% by weight.

9. The composition of claim 1 wherein the carrier is selected from the group consisting of an aqueous gel, anhydrous gel, a water-in-oil emulsion, an oil-in-water emulsion, purified water, dimethicone, triethanol amine, phenoxyethanol, benzene free carbomer, methylparaben, isopropylparaben, isobutylparaben, and butylparaben.

10. The composition of claim 9 wherein the carrier further comprises an emollient, a neutralizer-thickener, a preservative or mixtures thereof.

11. The composition of claim 9 further comprising a vitamin or a sunscreen.

12. The composition of claim 11 wherein the vitamin is selected from the group consisting of A, E, C, D, F, $CoQ_{10}$ and combinations thereof.

13. The composition of claim 11 wherein the sun screen is selected from the group consisting of p-aminobenzoic acid (PABA), paraben, digalloyl trioleate, dioxybenzone, ethyldihydroxy propyl PABA, ethylhexyl p-methoxycinnamate, ethylhexyl salicylate, glyceryl PABA, homosalate, menthyl anthranilate, octocrylene, octyl methoxycinnamate, octyl salicylate, oxybenzone, octyl dimethyl PABA, red petrolatum, titanium dioxide and zinc oxide.

14. A method for treating skin discoloration in a subject comprising topically applying the composition of claim 1 to skin of the subject in need thereof.

15. The method of claim 14 wherein the skin discoloration is from excess pigmentation, light damage, physical trauma or disease.

16. The method of claim 14 wherein the skin discoloration is observed as dark circles in the face sub-orbital region.

17. The method of claim 14 wherein the applying is for a period sufficient to observe a decrease in the discoloration.

18. The method of claim 14 wherein the applying is once or twice daily.

19. The cosmetically acceptable composition in accordance with claim 1 wherein the pheniramine vasoconstrictor salt is pheniramine maleate.

20. The composition of claim 19 wherein the pheniramine maleate is 2-3% by weight.

21. A packaged formulation for use in improving the appearance of skin discoloration comprising the vasoconstrictor composition of claim 1 and instructions for use.

22. The cosmetically acceptable composition of claim 1 further comprising at least two vasoconstrictors selected from the group consisting of tetrahydrozoline, ephedrine, naphazoline, phenylephrine, and salts and mixtures thereof, wherein the total amount of the vasoconstrictors is about 1% to about 7.5% by weight.

23. The composition of claim 22 wherein pheniramine and tetrahydrozoline or salts thereof each comprise about 2.5% of the composition by weight.

24. A method for reducing or eliminating the appearance of dark circle discoloration in the suborbital region of the face comprising topically applying the composition of claim 1 to the skin in the suborbital region of the subject.

* * * * *